United States Patent [19]

Schrader et al.

[11] 3,948,631

[45] *Apr. 6, 1976

[54] PHOSPHORO-AMIDO-THIOATES

[75] Inventors: Gerhard Schrader, Wuppertal-Cronenberg; Ludwig Eue; Helmuth Hack, both of Cologne, all of Germany; Seiichi Hirane, Kokubunji, Japan; Masahiro Aya, Kodaira, Japan; Shigeo Kishino, Machida, Japan; Nobuo Fukazawa, Hachioji, Japan

[73] Assignee: Bayer Aktiengesellschaft, Leverkusen, Germany

[ * ] Notice: The portion of the term of this patent subsequent to Mar. 12, 1991, has been disclaimed.

[22] Filed: Aug. 1, 1973

[21] Appl. No.: 384,675

Related U.S. Application Data

[62] Division of Ser. No. 10,052, Feb. 9, 1970, Pat. No. 3,787,538.

[30] Foreign Application Priority Data

Feb. 8, 1969 Japan................................ 44-9106

[52] U.S. Cl. ................................................ 71/87
[51] Int. Cl.² .......................................... A01N 9/36
[58] Field of Search ........................................ 71/87

[56] References Cited

UNITED STATES PATENTS

| | | | |
|---|---|---|---|
| 3,472,920 | 10/1969 | Schrader et al. | 71/87 |
| 3,636,143 | 1/1972 | Schrader et al. | 260/954 |
| 3,705,929 | 12/1972 | Schrader et al. | 260/951 |
| 3,711,582 | 1/1973 | Schräder et al. | 260/954 |
| 3,740,209 | 6/1973 | Schrader et al. | 71/87 |
| 3,760,044 | 9/1973 | Schrader et al. | 260/954 |
| 3,796,560 | 3/1974 | Schrader et al. | 71/87 |

*Primary Examiner*—Lewis Gotts
*Assistant Examiner*—Catherine L. Mills
*Attorney, Agent, or Firm*—Burgess, Dinklage & Sprung

[57] ABSTRACT

Phosphoro-amido-thioates, i.e. O-alkyl-O-[2-nitro-4-(alkyl, alkoxy and chloro)-phenyl]-N-alkyl-phosphoro-amido-thioates and O-alkyl-O-[2-nitro-4-(optionally alkyl, alkoxy and chloro)-phenyl]-N-cycloalkyl-phosphoro-amido-thioates, or O-alkyl-O-[2-nitro-4-(alkyl, alkoxy and chloro)-phenyl]-N-alkyl-amido-thionophosphates and O-alkyl-O-[2-nitro-4-(optionally alkyl, alkoxy and chloro)-phenyl]-N-cycloalkyl-amido-thionophosphates, which possess herbicidal properties and which may be produced by conventional methods.

14 Claims, No Drawings

PHOSPHORO-AMIDO-THIOATES

The present invention relates to and has for its objects the provision for particular new phosphoro-amido-thioates, i.e. O-alkyl-O-[2-nitro-4-(alkyl, alkoxy and chloro)-phenyl]-N-alkyl-phosphoro-amido-thioates and O-alkyl-O-[2-nitro-4-(optionally alkyl, alkoxy and chloro)-phenyl]-N-cycloalkyl-phosphoro-amido-thioates, or O-alkyl-O-[2-nitro-4-(alkyl, alkoxy and chloro)-phenyl]-N-alkyl-amido-thiono-phosphates and O-alkyl-O-[2-nitro-4-(optionally alkyl, alkoxy and chloro)-phenyl]-N-cycloalkyl-amido-thionophosphates, which possess herbicidal properties, active compositions in the form of mixtures of such compounds with solid and liquid dispersible carrier vehicles, and methods for producing such compounds and for using such compounds in a new way, especially for combating weeds, undesired plants, and the like, with other and further objects becoming apparent from a study of the within specification and accompanying examples.

It is already known that pentachloro-phenol (A), which may be designated as PCP, and 2,4-dichloro-phenyl-4'-nitro-phenyl-ether (B), which may be designated as NIP, as well as 2-chloro-4,6-bis(ethylamino)-1,3,5-triazine (C), which may be designated as CAT or Simazin, possess herbicidal properties.

It is furthermore known from British Pat. No. 659,682 that amido-thionophosphoric acid esters of the formula

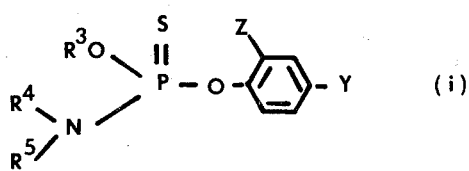

in which $R_3$ is an alkyl or alkenyl radical, $R_4$ is an alkyl radical, $R_5$ is an alkyl radical or a hydrogen atom, and one of Y and Z is a nitro radical and the other of Y and Z is a hydrogen atom or a nitro radical, possess insecticidal and fungicidal properties. In said British Patent, it is indicated only that such compounds have insecticidal and acaricidal activity as well as activity for the control of harmful fungi on plants, and that they can be used in the form of spray preparations. However, there is no actual test data showing their efficacy, and no indication that such compounds might have herbicidal activity. Furthermore, no mention is made of the applicability of such compounds to soil or of any reason to expect them to have herbicidal activity.

On the other hand, U.S. Pat. No. 3,074,790 describes compounds, for example O-(2,4-dichloro-phenyl)-O-methyl-N-isopropyl-phosphoro-amido-thioate (D), which have herbicidal properties.

In accordance with applicants' Japanese patent application No. 78104/66, it has been found that a certain derivative of this last-mentioned type of amido-thionophosphoric acid ester (which may be prepared in the same manner as the compounds of the present invention) has especially excellent herbicidal activity, to wit, O-(2-nitro-phenyl)-O-methyl-N-isopropyl-phosphoro-amido-thioate of the formula:

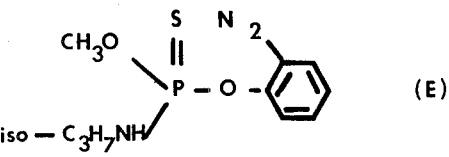

It has now been found, in accordance with the present invention, that the particular new phosphoro-amido-thioates, i.e. O-[2-nitro-4-(optionally alkyl, alkoxy and chloro)-phenyl]-O-alkyl-N-(alkyl or cycloalkyl)-phosphoro-amido-thioates, of the formula

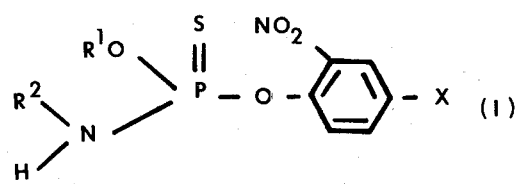

in which
$R^1$ is alkyl of 1–4 carbon atoms,
$R^2$ is alkyl of 3–6 carbon atoms or cycloakyl of 5–6 carbon atoms, and
when $R^2$ is alkyl of 3–6 carbon atoms, X is alkyl of 1–4 carbon atoms, alkoxy of 1–4 carbon atoms or chloro,
whereas
when $R^2$ is cycloalkyl of 5–6 carbon atoms, X is alkyl of 1–4 carbon atoms, alkoxy of 1–4 carbon atoms, chloro or hydrogen,
exhibit strong herbicidal, especially selective herbicidal properties.

It has been furthermore found, in accordance with process variant (a) of the present invention, that the compounds of formula (I) above may be produced by the process which comprises reacting an O-alkyl-N-alkyl or cycloalkyl-amido-thiono-phosphoric acid ester halide of the formula

in which

R¹ and R² are the same as defined above, and

Hal is a halogen atom such as chloro, bromo, iodo or fluoro, especially chloro, with a 2-nitro-4-substituted-phenol, preferably in the presence of an acid binding agent, or with a salt of the 2-nitro-4-substituted-phenol, correspoondingly of the formula

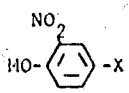 (III)

in which

X is the same as defined above, and

M is hydrogen, or a cation such as an ammonium or alkali metal cation, for example potassium, sodium, and the like.

Surprisingly, the particular new compounds of formula (I) above according to the present invention show both a higher and a more specific herbicidal effectiveness than the previously known compounds which are known to be usable for such purposes, e.g. compounds (A), (B) and (C) above. The instant compounds are especially effective as pre-emergence herbicides, and exhibit a remarkable effect in killing weeds, with only slight, if any, phytotoxic effect toward cultivated plants such as rice. The instant compounds therefore represent a valuable contribution to the art.

Advantageously, in accordance with the present invention, in the various formulae herein:

R¹ represents straight and branched chain lower alkyl hydrocarbon of 1–4 carbon atoms such as methyl, ethyl, n- and iso-propyl, n-, iso-, sec.- and tert.-butyl, and the like, especially $C_{1-3}$ or $C_{1-2}$ alkyl;

R² represents straight and branched chain alkyl hydrocarbon of 3–6 carbon atoms such as n- and iso-propyl, n-, iso-, sec.- and tert.-butyl, n- and iso-amyl, n- and iso-hexyl, and the like, especially $C_{4-6}$ or $C_{4-5}$ or $C_{3-4}$ alkyl, and more especially n-propyl and n-, iso- and sec.-butyl; or cycloalkyl hydrocarbon of 5–6 ring carbon atoms such as cyclopentyl, cyclohexyl, and the like, especially cyclohexyl; and X represents straight and branched chain lower alkyl hydrocarbon of 1–4 carbon atoms such as methyl to tert.-butyl inclusive as defined above, and the like, especially $C_{1-3}$ or $C_{1-2}$ alkyl;

straight and branched chain lower alkoxy of 1–4 carbon atoms such as methoxy, ethoxy, n- and iso-propoxy, n-, iso-, sec.- and tert.-butoxy, and the like, especially $C_{1-3}$ or $C_{1-2}$ alkoxy; or chloro; or in the case where R² is cycloalkyl of 5–6 ring carbon atoms, X may also be hydrogen.

Preferably, R¹ is $C_{1-3}$ or $C_{1-2}$ alkyl; R² is $C_{3-4}$ alkyl; or cyclohexyl; and X is $C_{1-3}$ or $C_{1-2}$ alkyl; or $C_{1-3}$ or $C_{1-2}$ alkoxy; or chloro; with the proviso that where R² is cyclohexyl, X is also hydrogen.

In particular, R¹ is $C_{1-3}$ alkyl; R² is n-propyl; or n-, iso- or sec.-butyl; or cyclohexyl; and when R² is alkyl (e.g. n-propyl or n-, iso- or sec.-butyl), X is $C_{1-2}$ alkyl; or $C_{1-2}$ alkoxy; or chloro; whereas when R² is cycloalkyl (e.g. cyclohexyl), X is hydrogen; or $C_{1-2}$ alkyl; or chloro.

More especially, the preferred compounds are those in which R¹ is $C_{1-3}$ alkyl, R² is straight or branched $C_{3-6}$ alkyl or $C_{5-6}$ cycloalkyl, and X is $C_{1-2}$ alkyl, $C_{1-2}$ alkoxy or chloro; or when R² is $C_{5-6}$ cycloalkyl, especially cyclohexyl, those in which X is $C_{1-2}$ alkyl, $C_{1-2}$ alkoxy, chloro or hydrogen; since these compounds are particularly effective as herbicides, especially when pre-emergence application is made to the soil, exhibiting markedly good effectiveness in killing weeds with little or no phytotoxicity to cultivated plants.

The reaction course according to process variant (a) is illustrated by the following formula scheme:

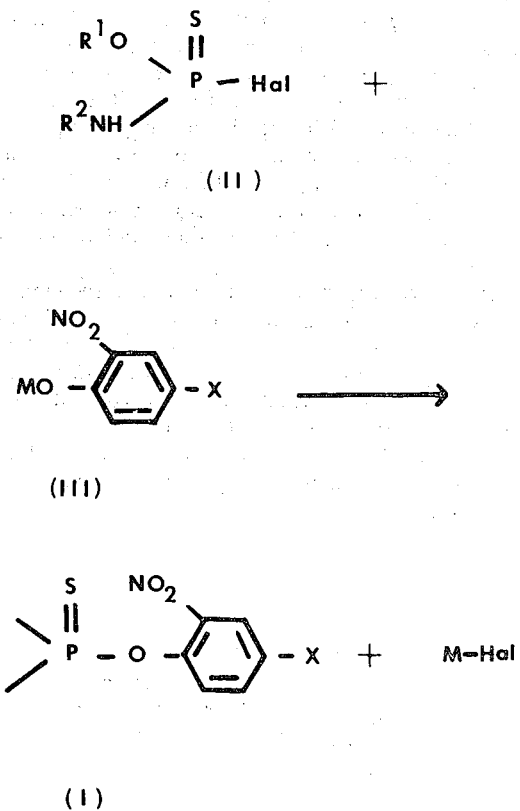

in which

R¹, R², X, Hal and M are the same as defined above.

The starting materials which may be used for reaction variant (a) are clearly characterized by formulae (II) and (III) above, and are well known or readily prepared.

In this regard, the O-alkyl-N-alkyl or cycloalkyl-amido-thionophosphoric acid ester halide starting material of formula (II) above may be synthesized according to the process illustrated by each of the following reaction schemes:

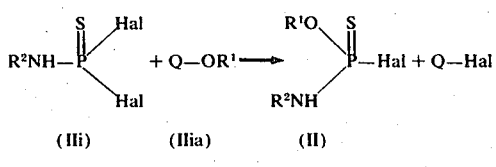

or

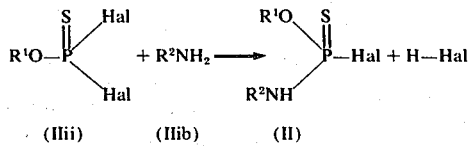

in which

Q is an alkali metal cation such as sodium and potassium, and

R¹, R² and Hal are the same as defined above.

Process variant (a) is preferably carried out in the presence of an inert organic solvent (this term includes a mere diluent). Examples of such solvents include aliphatic or aromatic hydrocarbons (which may be halogenated), for example benzine, methylene chloride, chloroform, carbon tetrachloride, benzene, chlorobenzene, toluene, and xylene; ethers, for example diethyl ether, dibutyl ether, dioxan, and tetrahydrofuran; aliphatic alcohols or ketones which have low boiling points, for example methanol, ethanol, isopropanol, acetone, methyl ethyl ketone, methyl isopropyl ketone, and methyl isobutyl ketone; and the like. Lower aliphatic nitriles, for example acetonitrile, propionitrile, and the like, may also be used.

If M is hydrogen in the appropriate starting compound of formula (III) above, the reaction according to variant (a) may preferably be carried out in the presence of an acid-binding agent. Examples of these include alkali metal carbonates and bicarbonates or alcoholates, such as potassium carbonate, sodium bicarbonate, sodium carbonate, or sodium or potassium methylate or ethylate, or aliphatic, aromatic or heterocyclic tertiary bases such as triethylamine, diethyl-aniline, pyridine, and the like. Instead of using an acid-binding agent, a salt of the 2-nitro-4-substituted-phenol of formula (III) above may be prepared, preferably an alkali metal or ammonium salt, and then this salt may be reacted with the starting O-alkyl-N-alkyl or cycloalkyl-amido-thionophosphoric acid ester halide of formula (II) above.

The reaction according to process variant (a) may be carried out within a fairly wide temperature range, but in general at temperatures from substantially between about 30°–110°C, and preferably between about 40°–70°C.

The present invention also provides another process variant, i.e. variant (b), for producing the instant new compounds. In accordance with this process variant, an O-(2-nitro-4-substituted-phenyl)-N-alkyl or cycloalkyl-amido-thionophosphoric acid ester halide dissolved in an inert solvent, preferably alcohol, is reacted with an alcoholic solution of the appropriate alkali metal alcoholate. To complete the reaction, the reaction mixture may be heated at substantially from between about 30°–110°C, and preferably from between about 40°–70°C, for a short time and then excess alcohol may be removed by distillation under reduced pressure. The residue may be dissolved in a water immiscible solvent, preferably one of the aforementioned hydrocarbons or ethers, the solution being washed with diluted solution of alkali metal hydroxide or ammonia. After the organic layer has been dried, the solvent may be removed by distillation to give the desired compound as residue.

This method of variant (b) is illustrated by the following reaction scheme:

(b)

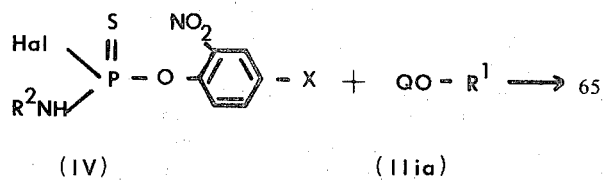

(IV)          (IIia)

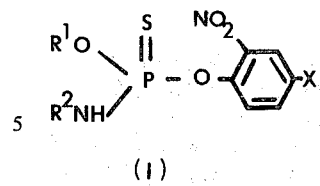

(I)

+ Q —Hal in which

R¹, R², X, Hal and Q are the same as defined above.

In accordance with process variant (b), the O-(2-nitro-4-substituted-phenyl)-N-alkyl or cyloalkyl-amido-thionophosphoric acid halide starting material may be synthesized according to a method illustrated by each of the following reaction schemes:

(b₁)

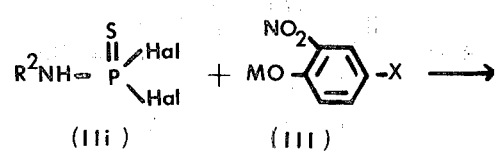

(IIi)          (III)

or (b₂)

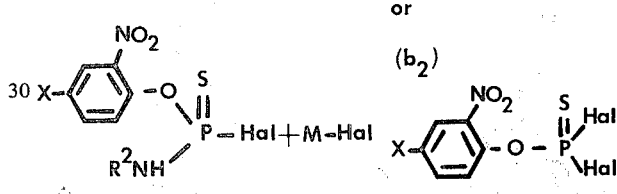

(IV)          (IVii)

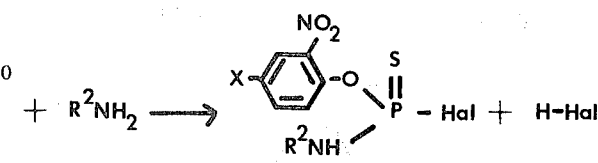

(IIib)          (IV)

in which

R², X and Hal are the same as defined above.

The present invention furthermore provides an alternative variant (c) to process variant (b), in which O-alkyl-O-(2-nitro-4-substituted-phenyl)-thionophosphoric acid ester halide dissolved in an inert solvent is reacted with the appropriate amine. This process variant (c) is illustrated by the following reaction scheme:

(c)

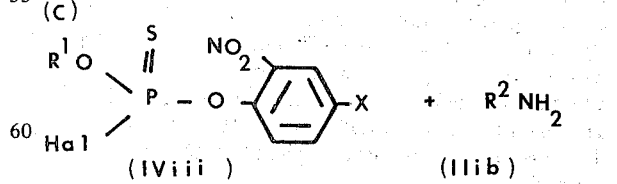

(IViii)          (IIIb)

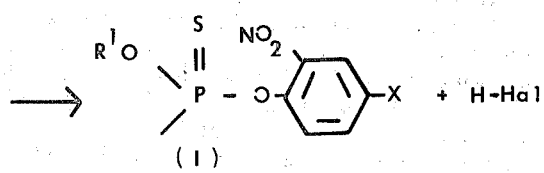

(I)

+ H—Hal in which
$R^1$, $R^2$, X and Hal are the same as defined above.

For this alternative variant (c), the O-alkyl-O-(2-nitro-4-substituted-phenyl)-thionophosphoric acid ester halide may be synthesized according to a method illustrated by each of the following reaction schemes ($c_1$)

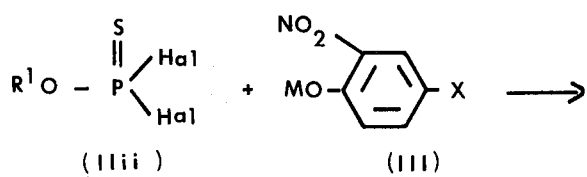

(IIii)    (III)

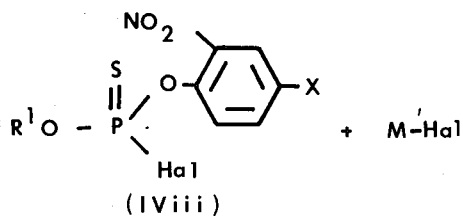

(IViii)

or ($c_2$)

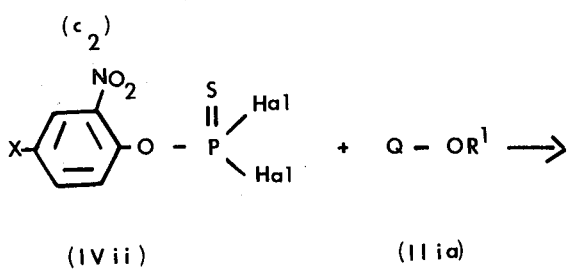

(IVii)    (IIia)

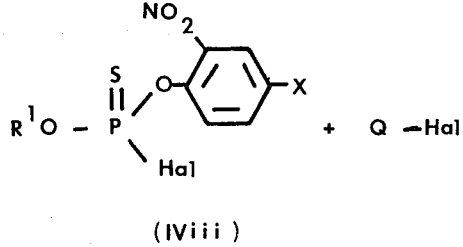

(IViii)

in which
$R^1$, X, Hal, M and Q are the same as defined above.

Advantageously, the instant active compounds exhibit a strong herbicidal potency and can therefore be used as germination inhibiting agents or weed-killers. By weeds in the sense used herein are meant all plants which grow in places where they are not desired. Whether the active compounds according to the present invention act as total or selective herbicidal agents depends on the amount applied, as the artisan will appreciate.

The active compounds according to the present invention can be used for example in the case of the following plants: dicotyledons, such as mustard (Sinapis), cress (Lepidium), catch weed (Galium), common chickweed (Stellaria), camomile (Matricaria), French weed (Galinsoga), goose-foot (Chenopodium), stinging nettle (Urtica), groundsel (Senecio), wild amaranth (Amaranthus), common purslane (Portulaca), cotton (Gossypium), beets (Beta), carrots Daucus), beans (Phaseolus), potatoes (Solanum), coffee (Coffea), cabbage (Brassica), spinach (Spinacia); monocotyledons, such as timothy (Phleum), meadowgrass (Poa), fescue (Festuca), finger grass (Digitaria), goosegrass (Eleusine), green foxtail (Setaria), raygrass (Lolium), cheat or brome grass (Bromus), barnyard grass (Echinochloa), maize (Zea), rice (Oryza), oats (Avena), barley (Hordeum), wheat (Triticum), millet (Panicum) and sugar cane (Saccharum); and the like.

The instant compounds are preferably used as selective herbicides and especially when applied to soil before germination, although they exhibit a particularly good selectivity when applied before and after emergence, e.g. in upland and paddy fields where mustard, cress, cotton, sugar beets, carrots, beans, potatoes, coffee, cabbage, spinach, maize, rice, oats, barley, wheat, millet and sugar cane are cultivated.

Significantly, the active compounds of the present invention are distinguished by the fact that they have little or no phytotoxicity to rice plants or other cultivated plants although they are markedly effective in small dosages as compared with PCP and NIP, i.e. compounds (A) and (B), etc. which have hitherto been used widely as herbicides in paddy fields. Furthermore, the same effect as with CAT or Simazin, i.e. compound (C), is generally achievable using the instant active compounds without any harm to crops, e.g. when applied to soil before germination for controlling weeds in upland fields. Especially when applied to soil before germination, the instant compounds are far better than the already known herbicides in that such instant compounds show a superior selective herbicidal activity, depending on the amount applied, with little or no phytotoxicity to cultivated plants.

The active compounds according to the present invention significantly also show a secondary insecticidal and fungicidal activity, e.g. against insects and phytopathogenic fungi which infest plants.

The active compounds according to the instant invention can be utilized, if desired, in the form of the usual formulations or compositions with conventional inert (i.e. plant compatible or herbicidally inert) pesticide diluents or extenders, i.e. diluents or extenders of the type usable in conventional pesticide formulations or compositions, e.g. conventional pesticide dispersible carrier vehicles, such as solutions, emulsions, suspensions, emulsifiable concentrates, spray powders, pastes, soluble powders, dusting agents, granules, etc. These prepared in known manner, for instance by extending the active compounds with conventional pesticide dispersible liqiud diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: inert dispersible liquid diluent carriers including inert organic solvents such as aromatic hydrocarbons (e.g. benzene, toluene, xylene, etc.), halogenated, especially chlorinated, aromatic hydrocarbons (e.g. chloro-benzenes), paraffins (e.g. petroleum fractions), chlorinated aliphatic hydrocarbons (e.g. methylene chloride, etc.), alcohols (e.g. methanol, ethanol, propanol, butanol, etc.), ether, ether-alcohols (e.g. glycol monomethyl ether, etc.), amines (e.g. ethanol-amine, etc.), amides (e.g. dimethyl formamide, etc.), sulfoxides (e.g. dimethyl sulfoxide, etc.), ketones (e.g. acetone, etc.), and/or water; as well as inert dispersible finely divided solid carriers, such as ground natural minerals (e.g. kaolins, alumina, silica, chalk, i.e. calcium carbonate, talc, kieselguhr, montmorillonite, clay, etc.), and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfonates, aryl sulfonates, etc., and especially alkyl aryl-polyglycol ethers, magnesium stearate, sodium oleate, etc.); and/or dispersing agents, such as lignin, sulfite waste liquors, methyl cellulose, etc.

As will be appreciated by the artisan, the active compounds according to the instant invention may be employed alone or in the form of mixtures with one another and/or with such solid and/or liquid dispersible carrier vehicles such as spreaders, wetting agents, adhesive agents, etc., and/or with other known compatible active agents, especially plant protection agents, such as other herbicides, or fungicides, insecticides, acaricides, nematocides, bactericides, plant growth regulators, soil disinfectants, including phenoxy compounds, chlorophenol compounds carbamates, diphenyl ethers, ureas, triazine compounds, and other known agricultural chemicals and/or fertilizers, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1 and 95% by weight, and preferably 0.5 and 90% by weight, of the mixture, whereas carrier composition mixtures suitable for direct application or field application generally contemplate those in which the active compound is present in an amount substantially between about 0.005–10% preferably 0.008–5%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.005–95%, and preferably 0.008–95%, by weight of the mixture.

In particular, the amount of active compound applied per unit area varies according to the purpose intended, i.e. the effect desired, and the mode of application. In general, higher quantities of substantially between about 5–40, especially 6–40, kg of active compound per hectare are applied for total or non-selective herbicidal activity, whereas lower quantities of substantially between about 1.25–5 kg. of active compound per hectare are applied for selective herbicidal activity, although such active compound may be applied generally in amounts of 1.25–40 kg per hectare.

The active compounds can also be used in accordance with the well-known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 1 quart/acre, preferably 2–16 fluid ounces/acre, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

While the active compounds can be used particularly effectively according to the pre-emergence method, they are also effective when used according to the post-emergence method.

Especially when application is carried out mainly before the germination of cultivated plants, the general conditions of cultivation are not so important, but the quantity of active compound to be applied per unit area and the application method are important, as the artisan will appreciate.

Furthermore, the present invention contemplates methods of selectively killing, combatting or controlling undesired plants, e.g. weeds and the like, which comprise applying to at least one of (a) such weeds and (b) their habitat, i.e. the locus to be protected, a herbicidally effective or toxic amount of the particular compound of the invention alone or together with a carrier vehicle as noted above. The instant formulations or compositions are applied in the usual manner, for example by spraying, atomizing, scattering, dusting, watering, sprinkling, and the like, whether for pre-emergence application to the soil or post-emergence application to the weeds.

It will be realized, of course, that in connection with the pre-emergence use of the instant compounds as well as the post-emergence use thereof, the concentration of the particular active compound utilized in admixture with the carrier vehicle will depend upon the intended application and may be varied within a fairly wide range depending upon the weather conditions, the soil, the purpose for which the active compound is used, e.g. for total or only selective herbicidal effect, and the plants which are to be controlled or protected. Therefore, in special cases, it is possible to go above or below the aforementioned concentration ranges and ranges of amounts per unit area.

The following illustrate, without limitation, examples of formulations which may be used in accordance with the present invention.

Formulation A

5% weight of instant compound (1), and 95% by weight of a mixture of talc and clay (3:1) are formulated into a dust by mixing and crushing, and applied by dusting to weeds and/or their habitat.

Formulation B

20% by weight of instant compound (10), 75% by weight of a mixture of talc and clay (3:2), 3% by weight of sodium alkylbenzene sulfonate, and 2% by weight of sodium dinaphthylalkylbenzene sulfonate, and 2% by weight of sodium dinaphthylmethane disulfonate are formulated into a wettable powder by mixing and crushing, and applied diluted with water at the concentration of 1 to 1,000 by spraying to weeds and/or their habitat.

Formulation C

20% by weight of instant compound (13), 75% by weight of xylol, and 5% by weight of the emulsifier Sorpol (trade name of the product of Toho Kagaku Kogyo K. K., Japan: polyoxyethylenealkylarylether) are formulated into an emulsifiable concentrate by mixing and stirring, and applied diluted with water at the concentration of 1 to 1,000 by spraying to weeds and/or their habitat.

Formulation D

Instant compound (19) is dissolved in xylol with heating, and the solution is sprayed onto clay granules while rotating and mixing so that about 10: by weight of the active compound is contained thereon. The granular formulation is applied as such by scattering on the surface of soil.

The herbicidal effectiveness of the particular new compounds of the present invention is illustrated without limitation, by the following Examples:

EXAMPLE 1

Test against weeds of paddy fields
Preparation of active compounds:

| | |
|---|---|
| Carrier vehicle | 5 parts by weight of acetone or 5 parts by weight of talc |
| Emulsifier | 1 part by weight of benzyloxypolyglycolether |

To produce a suitable preparations of the particular active compound, 1 part by weight of such active compound is throughly mixed with either one of the stated amounts of carrier vehicle and the stated amount of emulsifier. A resulted emulsifiable concentrate or a wettable powder is then diluted with water to a desired final concentration.

Test method:

Pots of 1/5,000 a, are charged with paddy field soil and then filled with water. Paddy rice seedlings (Kinmaze variety) of 3 to 4 leaves stage are transplanted into the pots under irrigated conditions. After the seedlings have taken root, seeds of barnyardgrass and broad-leaved weeds are sown and spikerush are planted in such pots simultaneously.

The preparations of the given active compound are sprayed at the rate of 500, 250 and 125 g of active compound per 10 a. of pot soil. After 3 weeks, the herbicidal effect against the barnyardgrass, spikerush and broad-leaved weeds and the phytotoxicity to the paddy rice are determined in accordance with the following scales:

| Herbicidal efficacy | | Phytotoxicity | |
|---|---|---|---|
| 5 | Plants are completely dead or no germination occurs | 5 | Plants are completely dead |
| 4 | Plants are partially destroyed or 20% or less germinated | 4 | Remarkable damage |
| 3 | Plants are remarkably damaged or 50% or less germinated | 3 | Marked damage |
| 2 | Plants are markedly damaged or 70% or less germinated | 2 | Small damage |
| 1 | Plants are slightly damaged or 90% or less germinated | 1 | Slight damage |
| 0 | No effect | 0 | No phytotoxicity |

The particular active compounds tested and the results obtained can be seen from the following Table 1.

Table 1

Herbicidal effect against weeds of paddy fields and phytotoxicity to rice

| Active Compound No. | Amount of active compound in g/10 a. | Herbicidal effect | | | Phytotoxicity |
|---|---|---|---|---|---|
| | | barnyard-grass | spikerush | broad-leaved weeds | rice |
| Compounds of Invention | | | | | |
| (1₁) | 500 | 5 | 5 | 5 | 0 |
| | 250 | 5 | 5 | 5 | 0 |
| | 125 | 5 | 4 | 4–5 | 0 |
| (2₁) | 500 | 5 | 5 | 5 | 0 |
| | 250 | 5 | 4–5 | 5 | 0 |
| | 125 | 5 | 4 | 5 | 0 |
| (3₁) | 500 | 5 | 5 | 5 | 0 |
| | 250 | 5 | 4 | 5 | 0 |
| | 125 | 5 | 3–4 | 4–5 | 0 |
| (4₁) | 500 | 5 | 5 | 5 | 0 |
| | 250 | 5 | 4–5 | 5 | 0 |
| | 125 | 4 | 4 | 4–5 | 0 |
| (5₁) | 500 | 5 | 5 | 5 | 0 |
| | 250 | 5 | 4–5 | 5 | 0 |
| | 125 | 5 | 4 | 4 | 0 |
| (6₁) | 500 | 5 | 5 | 5 | 0 |
| | 250 | 5 | 4 | 5 | 0 |
| | 125 | 5 | 3–4 | 4 | 0 |
| (7₁) | 500 | 5 | 5 | 5 | 0 |
| | 250 | 5 | 4–5 | 5 | 0 |
| | 125 | 4 | 4 | 4–5 | 0 |
| (8₁) | 500 | 5 | 5 | 5 | 0 |
| | 250 | 5 | 4 | 5 | 0 |
| | 125 | 5 | 3–4 | 4 | 0 |

Table 1-continued

Herbicidal effect against weeds of paddy fields and phytotoxicity to rice

| Active Compound No. | Amount of active compound in g/10 a. | Herbicidal effect | | | Phytotoxicity |
|---|---|---|---|---|---|
| | | barnyard-grass | spikerush | broad-leaved weeds | rice |
| ($9_1$) | 500 | 5 | 5 | 5 | 0 |
| | 250 | 5 | 4 | 5 | 0 |
| | 125 | 5 | 3 | 4 | 0 |
| ($10_1$) | 500 | 5 | 5 | 5 | 0 |
| | 250 | 5 | 5 | 5 | 0 |
| | 125 | 5 | 4–5 | 5 | 0 |
| ($11_1$) | 500 | 5 | 5 | 5 | 0 |
| | 250 | 5 | 4 | 5 | 0 |
| | 125 | 5 | 3 | 4 | 0 |
| ($12_1$) | 500 | 5 | 5 | 5 | 0 |
| | 250 | 5 | 4 | 5 | 0 |
| | 125 | 5 | 4 | 4–5 | 0 |
| ($13_1$) | 500 | 5 | 5 | 5 | 0 |
| | 250 | 5 | 5 | 5 | 0 |
| | 125 | 5 | 4–5 | 5 | 0 |
| ($14_1$) | 500 | 5 | 5 | 5 | 0 |
| | 250 | 5 | 5 | 5 | 0 |
| | 125 | 5 | 4–5 | 5 | 0 |
| ($15_1$) | 500 | 5 | 5 | 5 | 0 |
| | 250 | 5 | 4 | 5 | 0 |
| | 125 | 5 | 4 | 4 | 0 |
| ($16_1$) | 500 | 5 | 5 | 5 | 0 |
| | 250 | 5 | 4–5 | 5 | 0 |
| | 125 | 5 | 4–5 | 4–5 | 0 |
| ($17_1$) | 500 | 5 | 5 | 5 | 0 |
| | 250 | 5 | 4–5 | 5 | 0 |
| | 125 | 5 | 4 | 4–5 | 0 |
| ($18_1$) | 500 | 5 | 5 | 5 | 0 |
| | 250 | 5 | 5 | 5 | 0 |
| | 125 | 5 | 4–5 | 5 | 0 |
| ($19_1$) | 500 | 5 | 5 | 5 | 0 |
| | 250 | 5 | 5 | 5 | 0 |
| | 125 | 5 | 4–5 | 5 | 0 |
| ($20_1$) | 500 | 5 | 5 | 5 | 0 |
| | 250 | 5 | 4–5 | 5 | 0 |
| | 125 | 5 | 4 | 4–5 | 0 |
| ($21_1$) | 500 | 5 | 5 | 5 | 0 |
| | 250 | 5 | 4–5 | 5 | 0 |
| | 125 | 5 | 4 | 4–5 | 0 |
| ($22_1$) | 500 | 5 | 5 | 5 | 0 |
| | 250 | 5 | 4 | 5 | 0 |
| | 125 | 5 | 4 | 4 | 0 |
| ($23_1$) | 500 | 5 | 5 | 5 | 0 |
| | 250 | 5 | 4 | 5 | 0 |
| | 125 | 5 | 4 | 4 | 0 |
| ($24_1$) | 500 | 5 | 5 | 5 | 0 |
| | 250 | 5 | 4 | 5 | 0 |
| | 125 | 5 | 4 | 4 | 0 |
| ($25_1$) | 500 | 5 | 5 | 5 | 0 |
| | 250 | 5 | 4 | 5 | 0 |
| | 125 | 5 | 4 | 4 | 0 |
| Known Compounds-Comparison | | | | | |
| (A) pentachlorophenol | 500 | 5 | 3 | 5 | 0 |
| | 250 | 3 | 0 | 2 | 0 |
| | 125 | 1 | 0 | 0 | 0 |
| (B) 2,4-dichlorophenyl-4'-nitrophenyl ether | 500 | 5 | 5 | 5 | 3 |
| | 250 | 5 | 5 | 5 | 1 |
| | 125 | 3 | 1 | 2 | 0 |
| Control | — | 0 | 0 | 0 | 0 |

NOTES:
1) Broad-leaved weeds are Monochria vaginalis, Rotala indica, Lindernia pyxidaria, Dopatrium junceum, etc.
2) Compounds of invention have corresponding numbers to those in Table 4 below

EXAMPLE 2

Test against weeds of upland fields
Preparation of the active compounds:

| | |
|---|---|
| Carrier vehicle | 5 parts by weight of acetone or 5 parts by weight of talc |
| Emulsifier | 1 part by weight of benzyloxy-polyglycolether |

To produce a suitable preparation of the particular active compound, 1 part by weight of such active compound is throughly mixed with either one of the stated amounts of carrier vehicle and the stated amount of emulsifier. A resulted emulsifiable concentrate or a wettable powder is then diluted with water to a desired final concentration.

Test method:

After filling up pots of 30 × 30 cm with soil of diluvial volcanic ash, seeds of the below-mentioned weeds, upland rice (Hataminori variety) and vegetables are sown. After covering with soil, the preparations of a particular active compound are sprayed on the surface of the soil at the rate of 400, 200 and 100 g of active compound per 10 a. of pot soil. After 3 weeks, the herbicidal effect against various kinds of weeds and the phytotoxicity to upland rice and certain vegetables are determined in accordance with the following scales:

| Herbicidal efficacy | | Phytotoxicity | |
|---|---|---|---|
| 5 | Plants are completely dead or no germination occurs | 5 | Plants are completely dead or no germination occurs |
| 4 | Plants are partially destroyed after germination or 20% or less germinated | 4 | Plants are remarkably damaged after germination or 50% or less germinated |
| 3 | Plants are remarkably damaged after germination or 50% or less germinated | 3 | Plants are markedly damaged after germination or 70% or less germinated |
| 2 | Plants are markedly damaged after germination or 70% or less germinated | 2 | Plants are considerably damaged after germination or 70% or more germinated |
| 1 | Plants are slightly damaged after germination or 90% or less germinated | 1 | Plants are slightly damaged after germination or 90% or more germinated |
| 0 | No effect | 0 | No phytotoxicity |

The particular active compounds tested and the results obtained can be seen from the following Table 2.

Table 2

Herbicidal effect against weeds of upland fields and phytotoxicity to various crops

| Active Compound No. | Amount of active compound g/10 a. | Herbicidal effect | | | | | Phytotoxicity | | | | |
|---|---|---|---|---|---|---|---|---|---|---|---|
| | | barnyard-grass (Echinochloa) | finger-grass (Digitaria) | dent foxtail (Setaria) | wild amaranth (Amaranthus) | common purslane (Portulaca) | upland rice | Japanese radish | cucumber | tomato | carrot |
| Compounds of Invention | | | | | | | | | | | |
| (1₂) | 400 | 5 | 5 | 5 | 5 | 5 | 0 | 1 | 1 | 0 | 0 |
| | 200 | 5 | 5 | 5 | 5 | 5 | 0 | 0 | 0 | 0 | 0 |
| | 100 | 5 | 5 | 4 | 5 | 4–5 | 0 | 0 | 0 | 0 | 0 |
| (2₂) | 400 | 5 | 5 | 5 | 5 | 5 | 0 | 0 | 1 | 0 | 0 |
| | 200 | 5 | 5 | 5 | 5 | 5 | 0 | 0 | 0 | 0 | 0 |
| | 100 | 5 | 5 | 5 | 5 | 5 | 0 | 0 | 0 | 0 | 0 |
| (3₂) | 400 | 5 | 5 | 5 | 5 | 5 | 0 | 1 | 1 | 0 | 0 |
| | 200 | 5 | 5 | 5 | 5 | 5 | 0 | 0 | 0 | 0 | 0 |
| | 100 | 4 | 5 | 5 | 5 | 5 | 0 | 0 | 0 | 0 | 0 |
| (4₂) | 400 | 5 | 5 | 5 | 5 | 5 | 0 | 0 | 0 | 0 | 0 |
| | 200 | 5 | 5 | 5 | 5 | 5 | 0 | 0 | 0 | 0 | 0 |
| | 100 | 4 | 5 | 4–5 | 5 | 5 | 0 | 0 | 0 | 0 | 0 |
| (5₂) | 400 | 5 | 5 | 5 | 5 | 5 | 0 | 0 | 0 | 0 | 0 |
| | 200 | 4–5 | 5 | 5 | 5 | 5 | 0 | 0 | 0 | 0 | 0 |
| | 100 | 4 | 5 | 4–5 | 5 | 5 | 0 | 0 | 0 | 0 | 0 |
| (6₂) | 400 | 5 | 5 | 5 | 5 | 5 | 0 | 1 | 1 | 0 | 0 |
| | 200 | 5 | 5 | 5 | 5 | 5 | 0 | 0 | 0 | 0 | 0 |
| | 100 | 5 | 5 | 4 | 5 | 5 | 0 | 0 | 0 | 0 | 0 |
| (7₂) | 400 | 5 | 5 | 5 | 5 | 5 | 0 | 0 | 0 | 0 | 0 |
| | 200 | 5 | 5 | 5 | 5 | 5 | 0 | 0 | 0 | 0 | 0 |
| | 100 | 5 | 5 | 4–5 | 5 | 5 | 0 | 0 | 0 | 0 | 0 |
| (8₂) | 400 | 5 | 5 | 5 | 5 | 5 | 0 | 1 | 1 | 0 | 0 |
| | 200 | 5 | 5 | 4–5 | 5 | 5 | 0 | 0 | 0 | 0 | 0 |
| | 100 | 5 | 5 | 4 | 4 | 4–5 | 0 | 0 | 0 | 0 | 0 |
| (9₂) | 400 | 5 | 5 | 5 | 5 | 5 | 0 | 1 | 1 | 0 | 0 |
| | 200 | 5 | 5 | 5 | 5 | 5 | 0 | 0 | 0 | 0 | 0 |
| | 100 | 5 | 5 | 4 | 5 | 5 | 0 | 0 | 0 | 0 | 0 |
| (10₂) | 400 | 5 | 5 | 5 | 5 | 5 | 0 | 1 | 1 | 0 | 0 |
| | 200 | 5 | 5 | 5 | 5 | 5 | 0 | 0 | 0 | 0 | 0 |
| | 100 | 5 | 5 | 5 | 5 | 5 | 0 | 0 | 0 | 0 | 0 |
| (11₂) | 400 | 5 | 5 | 5 | 5 | 5 | 0 | 0 | 0 | 0 | 0 |
| | 200 | 5 | 5 | 5 | 5 | 5 | 0 | 0 | 0 | 0 | 0 |
| | 100 | 5 | 5 | 4–5 | 5 | 4–5 | 0 | 0 | 0 | 0 | 0 |
| (12₂) | 400 | 5 | 5 | 5 | 5 | 5 | 0 | 0 | 0 | 0 | 0 |
| | 200 | 5 | 5 | 5 | 5 | 5 | 0 | 0 | 0 | 0 | 0 |
| | 100 | 5 | 5 | 4–5 | 5 | 5 | 0 | 0 | 1 | 0 | 0 |
| (13₂) | 400 | 5 | 5 | 5 | 5 | 5 | 0 | 0 | 0 | 0 | 0 |
| | 200 | 5 | 5 | 5 | 5 | 5 | 0 | 0 | 0 | 0 | 0 |
| | 100 | 5 | 5 | 4–5 | 5 | 5 | 0 | 0 | 0 | 0 | 0 |
| (14₂) | 400 | 5 | 5 | 5 | 5 | 5 | 0 | 0 | 0 | 0 | 0 |
| | 200 | 5 | 5 | 5 | 5 | 5 | 0 | 0 | 0 | 0 | 0 |
| | 100 | 5 | 5 | 5 | 5 | 5 | 0 | 0 | 0 | 0 | 0 |
| (15₂) | 400 | 5 | 5 | 5 | 5 | 5 | 0 | 0 | 0 | 0 | 0 |
| | 200 | 5 | 5 | 5 | 5 | 5 | 0 | 0 | 0 | 0 | 0 |
| | 100 | 5 | 4–5 | 4–5 | 5 | 4–5 | 0 | 0 | 0 | 0 | 0 |
| (16₂) | 400 | 5 | 5 | 5 | 5 | 5 | 0 | 0 | 1 | 0 | 0 |
| | 200 | 5 | 5 | 5 | 5 | 5 | 0 | 0 | 0 | 0 | 0 |
| | 100 | 5 | 4–5 | 5 | 5 | 5 | 0 | 0 | 0 | 0 | 0 |
| (17₂) | 400 | 5 | 5 | 5 | 5 | 5 | 0 | 0 | 1 | 0 | 0 |
| | 200 | 5 | 5 | 5 | 5 | 5 | 0 | 0 | 0 | 0 | 0 |
| | 100 | 5 | 4–5 | 4–5 | 5 | 5 | 0 | 1 | 1 | 0 | 0 |
| (18₂) | 400 | 5 | 5 | 5 | 5 | 5 | 0 | 0 | 0 | 0 | 0 |
| | 200 | 5 | 5 | 5 | 5 | 5 | 0 | 0 | 0 | 0 | 0 |
| | 100 | 5 | 5 | 5 | 5 | 5 | 0 | 1 | 1 | 0 | 0 |
| | 400 | 5 | 5 | 5 | 5 | 5 | 0 | 1 | 1 | 0 | 0 |

Table 2-continued

| Active Compound No. | Amount of active compound g/10 a. | Herbicidal effect against weeds of upland fields and phytotoxicity to various crops | | | | | | | | | |
|---|---|---|---|---|---|---|---|---|---|---|---|
| | | Herbicidal effect | | | | | Phytotoxicity | | | | |
| | | barnyard-grass (Echinochloa) | finger-grass (Digitaria) | dent foxtail (Setaria) | wild amaranth (Amaranthus) | common purslane (Portulaca) | upland rice | Japanese radish | cucumber | tomato | carrot |
| ($19_2$) | 200 | 5 | 5 | 5 | 5 | 5 | 0 | 0 | 0 | 0 | 0 |
| | 100 | 5 | 5 | 5 | 5 | 5 | 0 | 0 | 0 | 0 | 0 |
| ($20_2$) | 400 | 5 | 5 | 5 | 5 | 5 | 0 | 1 | 1 | 0 | 0 |
| | 200 | 5 | 5 | 4 | 5 | 5 | 0 | 0 | 0 | 0 | 0 |
| | 100 | 5 | 4–5 | 3 | 5 | 4 | 0 | 0 | 0 | 0 | 0 |
| ($21_2$) | 400 | 5 | 5 | 5 | 5 | 5 | 0 | 1 | 1 | 0 | 0 |
| | 200 | 5 | 5 | 4 | 5 | 5 | 0 | 0 | 0 | 0 | 0 |
| | 100 | 5 | 4 | 3 | 4 | 4 | 0 | 0 | 0 | 0 | 0 |
| ($22_2$) | 400 | 5 | 5 | 5 | 5 | 5 | 0 | 1 | 1 | 0 | 0 |
| | 200 | 5 | 5 | 5 | 5 | 5 | 0 | 0 | 0 | 0 | 0 |
| | 100 | 5 | 4–5 | 4 | 4 | 4 | 0 | 0 | 0 | 0 | 0 |
| ($23_2$) | 400 | 5 | 5 | 5 | 5 | 5 | 0 | 0 | 0 | 0 | 0 |
| | 200 | 5 | 5 | 4 | 4 | 5 | 0 | 0 | 0 | 0 | 0 |
| | 100 | 5 | 4 | 4 | 4 | 4 | 0 | 0 | 0 | 0 | 0 |
| ($24_2$) | 400 | 5 | 5 | 5 | 5 | 5 | 0 | 1 | 1 | 0 | 0 |
| | 200 | 5 | 4 | 4 | 4 | 5 | 0 | 0 | 1 | 0 | 0 |
| | 100 | 5 | 4 | 3 | 4 | 4–5 | 0 | 0 | 0 | 0 | 0 |
| ($25_2$) | 400 | 5 | 5 | 5 | 5 | 5 | 0 | 1 | 1 | 0 | 0 |
| | 200 | 5 | 4 | 4 | 4 | 5 | 0 | 0 | 0 | 0 | 0 |
| | 100 | 5 | 4 | 4 | 4 | 4 | 0 | 0 | 0 | 0 | 0 |
| Known Compounds-Comparison | | | | | | | | | | | |
| (C) 2-chloro-4,6-bis(ethylamine)-1,3,5-triazine | 100 | 5 | 5 | 5 | 5 | 5 | 2 | 3 | 2 | 2 | 2 |
| | 50 | 4 | 4 | 5 | 5 | 5 | 0 | 1 | 1 | 1 | 1 |
| (B) 2,4-dichloro-phenyl-4'-nitrophenyl ether | 400 | 5 | 5 | 5 | 5 | 5 | 3 | 1 | 5 | 5 | 5 |
| | 200 | 5 | 5 | 4 | 5 | 5 | 0 | 0 | 2 | 2 | 3 |
| Control | — | 0 | 0 | 0 | 0 | 0 | 0 | 0 | 0 | 0 | 0 |

NOTE:
Compounds of invention have corresponding numbers to those in Table 4 below.

EXAMPLE 3

Test of pre-emergence soil treatment against various plants

To produce a suitable preparation of the particular active compound, 1 part by weight of such active compound is mixed with 5 parts by weight of solvent (acetone) and 1 part by weight of emulsifier (benzyloxypolyglycol ether), and the resulting emulsifiable concentrate is then diluted with water to the desired final concentration.

Seeds of the test plants are sown in normal soil and after 24 hours the preparation of the given active compound is sprayed onto the test plants. After 3 weeks, the degree of damage to the test plants is determined and characterized by the values 0 to 5, which have the following meaning:

0 No effect
1 Slight damage or slight growth delay
2 Marked damage or growth delay
3 Remarkable damage or only 50% germinated
4 Plants are partially destroyed after germination or only 25% germinated
5 Plants are completely dead or no germination occurs.

The particular active compounds tested, their amount per unit area, and the results obtained can be seen from the following Table 3:

Table 3

| Active Compound No. | Amount of active compound in kg/ha. | Pre-emergence soil treatment against various plants | | | | | | | | | | | |
|---|---|---|---|---|---|---|---|---|---|---|---|---|---|
| | | wheat | barley | rice | cotton | maize | cabbage | barnyard-grass | common purslane | goose-foot | common chickweed | wild amaranth | finger grass |
| Known Compounds-Comparison | | | | | | | | | | | | | |
| (D) O-(2,4-dichloro-phenyl)-O-methyl-N-isopropyl-phosphoro-amido-thioate | 20 | 2–3 | 2–3 | 3 | 2 | 3 | 2–3 | 5 | 5 | 5 | 5 | 4 | 5 |
| | 10 | 1 | 1 | 1 | 1 | 2 | 1 | 5 | 4 | 5 | 5 | 3 | 5 |
| | 5 | 0 | 0 | 0 | 0 | 0 | 0 | 5 | 2 | 5 | 3 | 1 | 5 |
| | 2.5 | 0 | 0 | 0 | 0 | 0 | 0 | 4–5 | 0 | 3–4 | 1 | 0 | 4 |
| | 1.26 | 0 | 0 | 0 | 0 | 0 | 0 | 3 | 0 | 2 | 0 | 0 | 3 |
| (E) O-(2-nitrophenyl)-O-methyl-N-isopropyl-phosphoro-amido-thioate | 20 | 4 | 4 | 5 | 4 | 3 | 4–5 | 5 | 5 | 5 | 5 | 5 | 5 |
| | 10 | 1–2 | 2 | 3 | 2 | 2 | 2 | 5 | 5 | 5 | 5 | 5 | 5 |
| | 5 | 0 | 0 | 0 | 0 | 0 | 0 | 5 | 5 | 5 | 5 | 4–5 | 5 |
| | 2.5 | 0 | 0 | 0 | 0 | 0 | 0 | 5 | 4 | 4 | 4 | 3 | 4–5 |
| | 1.26 | 0 | 0 | 0 | 0 | 0 | 0 | 5 | 2 | 2 | 2 | 1 | 3 |
| Compounds of Invention | | | | | | | | | | | | | |

Table 3-continued

| Active Compound No. | Amount of active compound in kg/ha. | Pre-emergence soil treatment against various plants | | | | | | | | | | |
|---|---|---|---|---|---|---|---|---|---|---|---|---|
| | | wheat | bar-ley | rice | cot-ton | maize | cab-bage | barnyard-grass | common purs-lane | goose-foot | common chick-weed | wild ama-ranth | finger grass |
| | 20 | 5 | 5 | 4 | 5 | 5 | 5 | 5 | 5 | 5 | 5 | 5 | 5 |
| | 10 | 1–2 | 1–2 | 1–2 | 2 | 1–2 | 1–2 | 5 | 5 | 5 | 5 | 5 | 5 |
| (2₃) | 5 | 0 | 0 | 0 | 0 | 0 | 0 | 5 | 5 | 5 | 5 | 5 | 5 |
| | 2.5 | 0 | 0 | 0 | 0 | 0 | 0 | 5 | 5 | 5 | 5 | 5 | 5 |
| | 1.26 | 0 | 0 | 0 | 0 | 0 | 0 | 5 | 4–5 | 4–5 | 4–5 | 4–5 | 5 |
| | 20 | 5 | 5 | 4 | 5 | 5 | 5 | 5 | 5 | 5 | 5 | 5 | 5 |
| | 10 | 1–2 | 1–2 | 1–2 | 2 | 2 | 2 | 5 | 5 | 5 | 5 | 5 | 5 |
| (14₃) | 5 | 0 | 0 | 0 | 0 | 0 | 0 | 5 | 5 | 5 | 5 | 5 | 5 |
| | 2.5 | 0 | 0 | 0 | 0 | 0 | 0 | 5 | 5 | 5 | 5 | 5 | 5 |
| | 1.25 | 0 | 0 | 0 | 0 | 0 | 0 | 5 | 4–5 | 4–5 | 5 | 4 | 5 |
| | 20 | 5 | 5 | 5 | 5 | 5 | 5 | 5 | 5 | 5 | 5 | 5 | 5 |
| | 10 | 1–2 | 1–2 | 1–2 | 1–2 | 1–2 | 2 | 5 | 5 | 5 | 5 | 5 | 5 |
| (19₃) | 5 | 0 | 0 | 0 | 0 | 0 | 0 | 5 | 5 | 5 | 5 | 5 | 5 |
| | 2.5 | 0 | 0 | 0 | 0 | 0 | 0 | 5 | 5 | 5 | 5 | 5 | 5 |
| | 1.25 | 0 | 0 | 0 | 0 | 0 | 0 | 5 | 4–5 | 4–5 | 5 | 5 | 5 |
| | 20 | 5 | 5 | 5 | 5 | 5 | 5 | 5 | 5 | 5 | 5 | 5 | 5 |
| | 10 | 1–2 | 1–2 | 1 | 1–2 | 1–2 | 2 | 5 | 5 | 5 | 5 | 5 | 5 |
| (3₃) | 5 | 0 | 0 | 0 | 0 | 0 | 0 | 5 | 5 | 5 | 5 | 5 | 5 |
| | 2.5 | 0 | 0 | 0 | 0 | 0 | 0 | 5 | 5 | 5 | 5 | 5 | 5 |
| | 1.25 | 0 | 0 | 0 | 0 | 0 | 0 | 5 | 4–5 | 4–5 | 5 | 4–5 | 5 |

The test results described in the above-mentioned Table 3 show that the compounds of the present invention have excellent selective herbicidal effect without causing and phytotoxicity to cultivated crops when used in a suitable quantity (e.g. 1.25 kg – 5 kg of active compound per hectare). Especially excellent herbicidal effect is shown against barnyardgrass (Echinochloa), common purslane (Portulaca), goose-foot (Chenopodium), common chickweed (Stellaria), wild amaranth (Amaranthus), fingergrass (Digitaria), and the like.

The following further examples illustrate, without limitation, the process for producing the particular new compounds of the present invention.

Example 4 [reaction variant (a)]

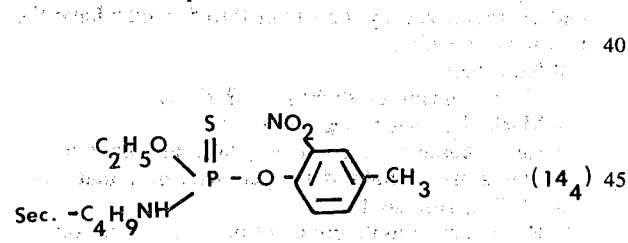

(14₄)

15.3 g (0.1 mol) of 2-nitro-4-cresol are dissolved in 100 ml of acetonitrile and 14.0 g of anhydrous potassium carbonate are added to the resulting solution. 21.6 g (0.1 mol) of O-ethyl-N-sec.-butyl-amide-thionophosphoric acid ester chloride are added dropwise thereto at 50 –60°C, with vigorous stirring. The mixture is further stirred at 70°C for 5 hours to complete the reaction. The inorganic salt produced is filtered off and the filtrate is distilled to remove the solvent. The residue is dissolved in 100 ml of benzene and the benzene solution is washed with 1% aqueous solution of sodium carbonate, and then dried over anhydrous sodium sulfate. After distilling off the benzene and recrystallizing the residue from a carbon tetrachloride/n-hexane mixture, 27 g of O-(2-nitro-4-methyl-phenyl)-O-ethyl-N-sec.-butyl-phosphoro-amido-thioate, an oily substance with the refractive index $n_D^{20}$ 1.5275, are obtained.

In an analogous manner, O-(2-nitro-4-ethyl-phenyl)-O-ethyl-N-sec.-butyl-phosphoro-amido-thioate (16₃), $n_D^{20}$ 1.5252, O-(2-nitro-4-methoxy-phenyl)-O-ethyl-N-sec.-butyl-phosphoro-amido-thioate (17₃), $n_D^{20}$ 1.5328, and O-(2-nitro-4-chloro-phenyl)-O-ethyl-N-sec.-butyl-phosphoro-amido-thioate (19₄), $n_D^{20}$ 1.5414, are obtained when 2-nitro-4-ethyl-phenol, 2-nitro-4-methoxy-phenol and 2-nitro-4-chloro-phenol are used, respectively, instead of 2-nitro-4-cresol, and these compounds have similar herbicidal activity.

Example 5 [reaction variant (a)]

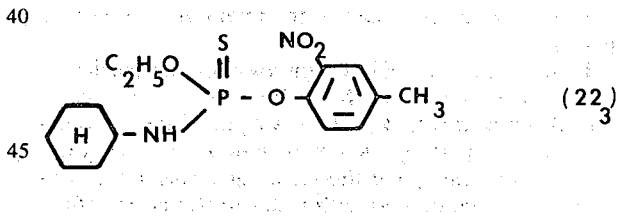

(22₃)

76.7 g (0.5 mol) of 2-nitro-4-cresol are dissolved in 400 ml of acetonitrile and 80 g of dried and sifted anhydrous potassium carbonate are added to the resulting solution. 121 g (0.5 mol) of O-ethyl-N-cyclohexyl-amido-thionophosphoric acid ester chloride are added dropwise thereto at 50° – 60°C, with vigorous stirring. The mixture is further heated at 70°C for 3 hours to complete the reaction. The inorganic salt produced is filtered off and the filtrate is distilled to remove the solvent. The residue is dissolved in 100 ml of benzene. The benzene solution is washed with a 1% aqueous solution of sodium carbonate and then dried over anhydrous sodium sulfate. After distilling off the benzene and recrystallizing the residue from a carbon tetrachloride/n-hexane mixture, 143 g of O-(2-nitro-4-methyl-phenyl)-O-ethyl-N-cylcohexyl-phosphoro-amido-thioate are obtained. M.p. 75°–76°C.

In an analogous manner, O-(2-nitro-phenyl)-O-ethyl-N-cylcohexyl-phosphoro-amido-thioate (20₃), $n_D^{20}$ 1.5489, O-(2-nitro-4-ethyl-phenyl)-O-ethyl-N-cyclohexyl-phosphoro-amido-thioate (23₃), $n_D^{20}$ 1.5430, and O-(2-nitro-4-chloro-phenyl)-O-ethyl-N-cyclohexyl-phosphoro-amido-thioate (25₃), m.p. 88° – 90°C, having similar herbicidal activity, are obtained when the corresponding 2-nitro-phenol, 2-nitro-4-ethyl-phenol and 2-nitro-4-chloro-phenol are used instead of 2-nitro-4-cresol.

The following Table 4 illustrates appropriate data for typical compounds of the present invention.

Table 4

| Compound No. | Structural formula | Chemical Name | Physical Property |
|---|---|---|---|
| (1₃) | CH₃O, n-C₃H₇NH / P(=S) - O - C₆H₃(NO₂)- CH₃ | O-(2-nitro-4-methyl-phenyl)-O-methyl-N-n-propyl-phosphoro-amido-thioate | m.p. 50–52°C |
| (2₃) | C₂H₅O, n-C₃H₇NH / P(=S) - O - C₆H₃(NO₂)- CH₃ | O-(2-nitro-4-methyl-phenyl)-O-ethyl-N-n-propyl-phosphoro-amido-thioate | $n_D^{20}$ 1.5394 |
| (3₃) | CH₃O, n-C₃H₇NH / P(=S) - O - C₆H₃(NO)- Cl | O-(2-nitro-4-chloro-phenyl)-O-methyl-N-n-propyl-phosphoro-amido-thioate | m.p. 52–54°C |
| (4₃) | C₂H₅O, n-C₃H₇NH / P(=S) - O - C₆H₃(NO₂)- Cl | O-(2-nitro-4-chloro-phenyl)-O-ethyl-N-n-propyl-phosphoro-amido-thioate | m.p. 39–41°C |
| (5₃) | CH₃O, n-C₄H₉NH / P(=S) - O - C₆H₃(NO₂)- CH₃ | O-(2-nitro-4-methyl-phenyl)-O-methyl-N-n-butyl-phosphoro-amido-thioate | $n_D^{20}$ 1.5409 |
| (6₃) | C₂H₅O, n-C₄H₉NH / P(=S) - O - C₆H₃(NO₂)- CH₃ | O-(2-nitro-4-methyl-phenyl)-O-ethyl-N-n-butyl-phosphoro-amido-thioate | $n_D^{20}$ 1.5352 |
| (7₃) | CH₃O, n-C₄H₉NH / P(=S) - O - C₆H₃(NO₂)- Cl | O-(2-nitro-4-chloro-phenyl)-O-methyl-N-n-butyl-phosphoro-amido-thioate | $n_D^{20}$ 1.5500 |
| (8₃) | C₂H₅O, n-C₄H₉NH / P(=S) - O - C₆H₃(NO₂)- Cl | O-(2-nitro-4-chloro-phenyl)-O-ethyl-N-n-butyl-phosphoro-amido-thioate | $n_D^{20}$ 1.5440 |
| (9₃) | CH₃O, iso-C₄H₉NH / P(=S) - O - C₆H₃(NO₂)- CH₃ | O-(2-nitro-4-methyl-phenyl)-O-methyl-N-isobutyl-phosphoro-amido-thioate | m.p. 62–64°C |
| (10₃) | C₂H₅O, iso-C₄H₉NH / P(=S) - O - C₆H₃(NO₂)- CH₃ | O-(2-nitro-4-methyl-phenyl)-O-ethyl-N-isobutyl-phosphoro-amido-thioate | $n_D^{20}$ 1.5330 |

Table 4-continued

| Compound No. | Structural formula | Chemical Name | Physical Property |
|---|---|---|---|
| (11₃) | CH₃O, iso-C₄H₉NH / P(S)-O-[2-NO₂, 4-Cl-phenyl] | O-(2-nitro-4-chloro-phenyl)-O-methyl-N-isobutyl-phosphoro-amido-thioate | m.p. 52–54°C |
| (12₃) | C₂H₅O, iso-C₄H₉NH / P(S)-O-[2-NO₂, 4-Cl-phenyl] | O-(2-nitro-4-chloro-phenyl)-O-ethyl-N-iso-butyl-phosphoro-amido-thioate | m.p. 41–43°C |
| (13₃) | CH₃O, sec.-C₄H₉NH / P(S)-O-[2-NO₂, 4-CH₃-phenyl] | O-(2-nitro-4-methyl-phenyl)-O-methyl-N-sec.-butyl-phosphoro-amido-thioate | m.p. 89–92°C |
| (14₅) | C₂H₅O, sec.-C₄H₉NH / P(S)-O-[2-NO₂, 4-CH₃-phenyl] | O-(2-nitro-4-methyl-phenyl)-O-ethyl-N-sec.-butyl-phosphoro-amido-thioate | $n_D^{20}$ 1.5275 |
| (15₃) | iso-C₃H₇O, sec.-C₄H₉NH / P(S)-O-[2-NO₂, 4-CH₃-phenyl] | O-(2-nitro-4-methyl-phenyl)-O-isopropyl-N-sec.-butyl-phosphoro-amido-thioate | $n_D^{20}$ 1.5225 |
| (16₄) | C₂H₅O, sec-C₄H₉NH / P(S)-O-[2-NO₂, 4-C₂H₅-phenyl] | O-(2-nitro-4-ethyl-phenyl)-O-ethyl-N-sec.-butyl-phosphoro-amido-thioate | $n_D^{20}$ 1.5252 |
| (17₄) | C₂H₅O, sec.-C₄H₉NH / P(S)-O-[2-NO₂, 4-OCH₃-phenyl] | O-(2-nitro-4-methoxy-phenyl)-O-ethyl-N-sec.-butyl-phosphoro-amido-thioate | $n_D^{20}$ 1.5328 |
| (18₃) | CH₃O, sec.-C₄H₉NH / P(S)-O-[2-NO₂, 4-Cl-phenyl] | O-(2-nitro-4-chloro-phenyl)-O-methyl-N-sec.-butyl-phosphoro-amido-thioate | m.p. 47–50°C |
| (19₅) | C₂H₅O, sec.-C₄H₉NH / P(S)-O-[2-NO₂, 4-Cl-phenyl] | O-(2-nitro-4-chloro-phenyl)-O-ethyl-N-sec.-butyl-phosphoro-amido-thioate | $n_D^{20}$ 1.5414 |
| (20₄) | C₂H₅O, cyclohexyl-NH / P(S)-O-[2-NO₂-phenyl] | O-(2-nitro-phenyl)-O-ethyl-N-cyclohexyl-phosphoro-amido-thioate | $n_D^{20}$ 1.5489 |
| (21₃) | CH₃O, cyclohexyl-NH / P(S)-O-[2-NO₂, 4-CH₃-phenyl] | O-(2-nitro-4-methyl-phenyl)-O-methyl-N-cyclohexyl-phosphoro-amido-thioate | m.p. 80–82°C |

Table 4-continued

| Compound No. | Structural formula | Chemical Name | Physical Property |
|---|---|---|---|
| (22₄) | | O-(2-nitro-4-methyl-phenyl)-O-ethyl-N-cyclohexyl-phosphoro-amido-thioate | m.p. 75–76°C |
| (23₄) | | O-(2-nitro-4-ethyl-phenyl)-O-ethyl-N-cyclohexyl-phosphoro-amido-thioate | $n_D^{20}$ 1.5430 |
| (24₃) | | O-(2-nitro-4-chloro-phenyl)-O-methyl-N-cyclohexyl-phosphoro-amido-thioate | m.p. 91–93°C |
| (25₄) | | O-(2-nitro-4-chloro-phenyl)-O-ethyl-N-cyclohexyl-phosphoro-amido-thioate | m.p. 88–90°C |

It will be realized by the artisan that all of the foregoing compounds contemplated by the present invention possess the desired selective or total herbicial properties, and especially the capability of selectively destroying weeds, as well as a comparatively low toxicity toward warmblooded creatures and a concomitantly low phytotoxicity with respect to higher plants, depending upon the amounts used, enabling such compounds to be used with correspondingly favorable compatibility with warm-blooded creatures and higher plants for more effective control and/or elimination of weeds by selective application of such compounds to such weeds and/or their habitat. Nevertheless, the instant compounds possess total herbicidal action when used in large quantities, although selective herbicidal action is obtained when used in smaller quantities. As contemplated herein, the term "weeds" is meant to include not only weeds in the narrow sense, but also in the broad sense, whereby to cover all plants and vegetation considered undesirable for the particular purposes in question.

It will be appreciated that the instant specification and examples are set forth by way of illustration and not limitation, and that various modifications and changes may be made without departing from the spirit and scope of the present invention which is to be limited only by the scope of the appended claims.

What is claimed is:

1. A herbicidal composition comprising a herbicidally effective amount of a phosphoro-amido-thioate of the formula

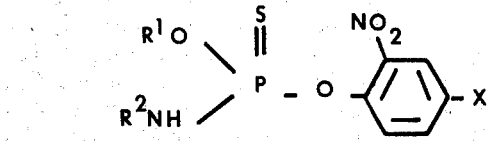

in which R¹ is alkyl of 1–4 carbon atoms, R² is selected from the group consisting of n-propyl, alkyl of 4–6 carbon atoms and cycloalkyl of 5–6 ring carbon atoms, and when R² is n-propyl or alkyl of 4–6 carbon atoms, X is selected from the group consisting of alkyl of 1–4 carbon atoms and chloro, whereas when R² is cycloalkyl of 5–6 carbon atoms, X is selected from the group consisting of alkyl of 1–4 carbon atoms, alkoxy of 1–4 carbon atoms, chloro and hydrogen, in admixture with a diluent.

2. A composition according to claim 1 wherein such compound is selected from the group consisting of:
O-(2-nitro-4-methyl-phenyl)-O-methyl-N-n-propyl-phosphoro-amido-thioate,
O-(2-nitro-4-methyl-phenyl)-O-ethyl-N-n-propyl-phosphoro-amido-thioate,
O-(2-nitro-4-chloro-phenyl)-O-methyl-N-n-propyl-phosphoro-amido-thioate,
O-(2-nitro-4-chloro-phenyl)-O-methyl-N-sec.-butyl-phosphoro-amido-thioate,
O-(2-nitro-4-methyl-phenyl)-O-ethyl-N-iso-butyl-phosphoro-amido-thioate,
O-(2-nitro-phenyl)-O-ethyl-N-cyclohexyl-phosphoro-amido-thioate, O-(2-nitro-4-methyl-phenyl)-O-methyl-N-cyclohexyl-phosphoro-amido-thioate, and
O-(2-nitro-4-chloro-phenyl)-O-ethyl-N-cylcohexyl-phosphoro-amidothioate, 3. A method of combating undesired vegetation which comprises applying thereto a herbicidally effective amount of a phosphoro-amido-thioate of the formula

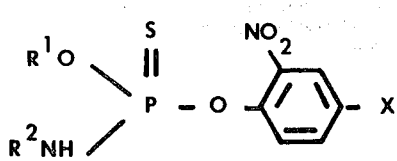

in which $R^1$ is alkyl of 1–4 carbon atoms, $R^2$ is selected from the group consisting of n-propyl, alkyl of 4–6 carbon atoms and cycloalkyl of 5–6 ring carbon atoms, and when $R^2$ is n-propyl or alkyl of 4–6 carbon atoms, X is selected from the group consisting of alkyl of 1–4 carbon atoms and chloro, whereas when $R^2$ is cycloalkyl of 5–6 carbon atoms, X is selected from the group consisting of alkyl of 1–4 carbon atoms, alkoxy of 1–4 carbon atoms, chloro and hydrogen.

4. The method according to claim 3 wherein $R^1$ is $C_{1-3}$ alkyl, $R^2$ is selected from the group consisting of n-propyl, $C_4$ alkyl and cyclohexyl, and when $R^2$ is n-propyl or $C_4$ alkyl, X is selected from the group consisting of $C_{1-3}$ alkyl and chloro, whereas when $R^2$ is cyclohexyl, X is selected from the group consisting of $C_{1-3}$ alkyl, $C_{1-3}$ alkoxy, chloro and hydrogen.

5. The method according to claim 3 wherein $R^1$ is $C_{1-3}$ alkyl, $R^2$ is selected from the group consisting of n-propyl, n-, iso- and sec.-butyl, and cyclohexyl, and when $R^2$ is selected from the group consisting of n-propyl, n-, iso- and sec.-butyl, X is selected from the group consisting of $C_{1-2}$ alkyl, and chloro, whereas when $R^2$ is cyclohexyl, X is selected from the group consisting of $C_{1-2}$ alkyl, chloro and hydrogen.

6. The method according to claim 3 wherein such compound is O-(2-nitro-4-methyl-phenyl)-O-methyl-N-n-propyl-phosphoro-amido-thioate of the formula

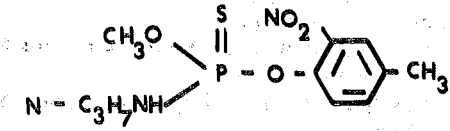

7. The method according to claim 3 wherein such compound is O-(2-nitro-4-methyl-phenyl)-O-ethyl-N-n-propyl-phosphoro-amido-thioate of the formula

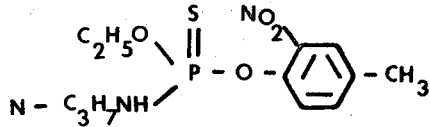

8. The method according to claim 3 wherein such compound is O-(2-nitro-4-chloro-phenyl)-O-methyl-N-n-propyl-phosphoro-amido-thioate of the formula

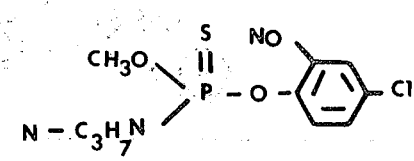

9. The method according to claim 3 wherein such compound is O-(2-nitro-4-chloro-phenyl)-O-methyl-N-sec.-butyl-phosphoro-amido-thioate of the formula

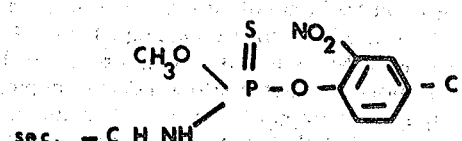

10. The method according to claim 3 wherein such compound is O-(2-nitro-4-methyl-phenyl)-O-ethyl-N-iso-butyl-phosphoro-amido-thioate of the formula

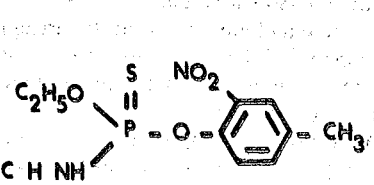

11. The method according to claim 3 wherein such compound is O-(2-Nitro-phenyl)-O-ethyl-N-cyclohexyl-phosphoro-amido-thioate of the formula

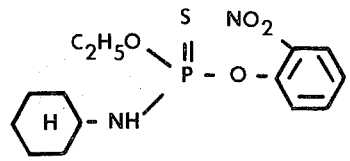

12. The method according to claim 3 wherein such compound is O-(2-nitro-4-methyl-phenyl)-O-methyl-N-cyclohexyl-phosphoro-amido-thioate of the formula

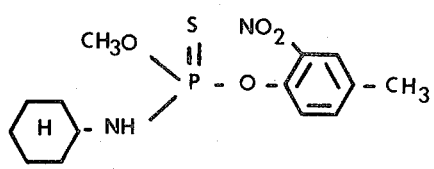

13. The method according to claim 3 wherein such compound is O-(2-nitro-4-chloro-phenyl)-O-ethyl-N-cyclohexyl-phosphoro-amido-thioate of the formula

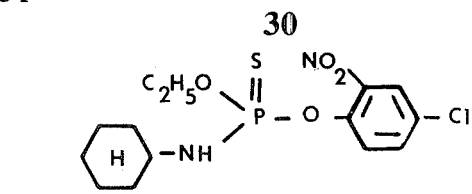

14. A method of combating undesired vegetation which comprises applying to the habitat prior to the emergence of said vegetation a herbicidally effective amount of a phosphoro-amido-thioate of the formula in which $R^1$ is alkyl of 1–4 carbon atoms, $R^2$ is selected from the group consisting of n-propyl, alkyl of 4–6 carbon atoms and cycloalkyl of 5–6 ring carbon atoms, and when $R^2$ is n-propyl or alkyl of 4–6 carbon atoms, X is selected from the group consisting of alkyl of 1–4 carbon atoms and chloro, whereas when $R^2$ is cycloalkyl of 5–6 carbon atoms, X is selected from the group consisting of alkyl of 1–4 carbon atoms, alkoxy of 1–4 carbon atoms, chloro and hydrogen.

* * * * *

UNITED STATES PATENT AND TRADEMARK OFFICE
CERTIFICATE OF CORRECTION

PATENT NO. : 3,948,631
DATED : April 6, 1976
INVENTOR(S) : Gerhard Schrader et al It is certified that error appears in the above-identified patent and that said Letters Patent are hereby corrected as shown below:

Col. 2, line 10, "N $_2$" should be -- $NO_2$ --;

Col. 3, line 6, "correspoondingly" should be --correspondingly--

Col. 28, line 65, "iso-C H NH" should be --iso-$C_4H_9$NH --.

Signed and Sealed this

Nineteenth Day of April 1977

[SEAL]

Attest:

RUTH C. MASON
Attesting Officer

C. MARSHALL DANN
Commissioner of Patents and Trademarks